United States Patent [19]

Giddings

[11] Patent Number: 5,141,651
[45] Date of Patent: Aug. 25, 1992

[54] PINCHED CHANNEL INLET SYSTEM FOR REDUCED RELAXATION EFFECTS AND SSTOPLESS FLOW INJECTION IN FIELD-FLOW FRACTIONATION

[75] Inventor: John C. Giddings, Salt Lake City, Utah

[73] Assignee: University of Utah, Salt Lake City, Utah

[21] Appl. No.: 617,927

[22] Filed: Nov. 21, 1990

Related U.S. Application Data

[63] Continuation of Ser. No. 365,171, Jun. 12, 1989, abandoned.

[51] Int. Cl.⁵ .................................................. B03B 5/00
[52] U.S. Cl. .................................... 210/748; 210/243; 210/513; 210/781; 210/800; 210/804; 209/18; 209/131; 209/156; 209/422
[58] Field of Search ..................... 209/1, 2, 112, 18, 39, 209/40, 127.1, 129, 131, 132, 155, 156, 208, 210, 213, 214, 223.1, 232, 422, 478, 493, 494; 210/222, 223, 243, 695, 748, 800, 804, 513, 781

[56] References Cited

U.S. PATENT DOCUMENTS

| 3,449,938 | 6/1969 | Giddings | 210/775 |
| 4,102,780 | 7/1978 | Sun et al. | 209/39 |
| 4,147,621 | 4/1979 | Giddings | 210/637 |
| 4,214,981 | 7/1980 | Giddings | 210/695 |
| 4,235,710 | 11/1980 | Sun | 209/213 |
| 4,284,489 | 8/1981 | Grant et al. | 209/155 |
| 4,737,268 | 4/1988 | Giddings | 210/748 |
| 4,830,756 | 5/1989 | Giddings | 210/748 |

FOREIGN PATENT DOCUMENTS 2317013  2/1977  France ............................. 210/695

Primary Examiner—W. Gary Jones
Attorney, Agent, or Firm—Terry M. Crellin

[57] ABSTRACT

A continuous flow FFF process for the separation of samples of particles which uses a modified channel structure to reduce the relaxation effect, reduce sample adhesion to the wall, and where possible eliminate the stop-flow procedure and thus greatly increase the speed and stability of operation, said modified channel comprises a thin channel whose thickness is reduced at the inlet end for a substantial distance beyond the inlet, such as the conventional triangular or near triangular piece, and then broadened out at the outlet end of the channel.

13 Claims, 5 Drawing Sheets

15 μm PS LATEX MICROSPHERES

STOP FLOW, UNIFORM CHANNEL

15 μm PS LATEX MICROSPHERES

STOPLESS FLOW, UNIFORM CHANNEL

15 μm PS LATEX MICROSPHERES

STOPLESS FLOW, PINCHED INLET CHANNEL 1

PINCHED CHANNEL INLET SYSTEM FOR REDUCED RELAXATION EFFECTS AND SSTOPLESS FLOW INJECTION IN FIELD-FLOW FRACTIONATION

Work on this invention was supported by funding from National Science foundation contract CHE 8800675.

This application is a continuation of application Ser. No. 07/365,171, filed Jun. 12, 1989, now abandoned.

BACKGROUND OF THE INVENTION

1. Field of the Invention

This invention relates to an improved process for the fractionation of particles. More particularly, the invention relates to a new field-flow fractionation (FFF) process which uses a modified channel structure to improved the speed and effectiveness of operation.

Specifically, the invention provides a modified continuous flow FFF process for the separation of samples of particles and macromolecules which uses a modified channel structure to reduce the relaxation effect, reduce sample adhesion to the wall, and where possible eliminate the stop-flow procedure and thus greatly increase the speed and stability of operation. The new process of the invention comprises an improvement in the FFF process wherein a carrier fluid containing the particles to be separated is forced through a thin flow channel having an inlet and outlet end and a field or gradient is used to induce a driving force acting across the thin dimension perpendicular to the flow axis and the particles entering the channel at the inlet end undergo a relaxation process and approach a steady state distribution within the channel, the improvement comprising using as the thin channel a thin channel whose thickness is reduced at the inlet end for a substantial distance beyond the inlet means, such as the conventional triangular or near triangular piece, and then broadened out at the outlet end.

The invention further provides an apparatus for conducing the above-described process.

2. Prior Art

There is a growing need in industry and health sciences for the separation and characterization of micron sized particles including biological cells, latices, environmental particles, industrial powders, crystallization products, and related particulate matter. There is also a growing need for the separation of submicron sized particles, macromolecules and synthetic polymers.

Various methods have been proposed, but in general, they have been too slow, complex in operation, inefficient and expensive or have failed to effect the separation with the desired degree of resolution needed for commercial operations.

Some of the highest resolutions techniques disclosed have been those based on field-flow fractionation (FFF) as disclosed in the following U.S. patents and copending patent applications: U.S. Pat. No. 3,449,938, U.S. Pat. No. 4,147,621, U.S. Pat. No. 4,214,981, U.S. Pat. No. 4,250,026, U.S. Pat. No. 4,737,268, and copending patent applications—Giddings—"Lif-Induced Hyperlayer Field-Flow Fractionation Process for Particle Separation" Ser. No. 153,774, filed Feb. 8, 1988, U.S. patent application—Giddings—"Process for Continuous Particle and Polymer Separation in Split-Flow thin Cells using Flow-Dependent Lift Forces", Ser. No. 194,851, filed May 17, 1988, U.S. patent application—Giddings—"High Speed Separation of Ultra-High Molecular Weight Polymers by Hyperlayer Field-Flow Fractionation" Ser. No. 217,707, filed Jul. 11, 1988, and U.S. patent application—Williams—"Process of Programming of Field-Flow Fractionation"—Ser. No. 237,188, filed Aug. 29, 1988.

Attempts have been made to improve the FFF process, such as disclosed in Giddings et al—Anal. Chem. 56 2099) 1984, which discloses a method for reducing disturbances at the triangular end piece by reducing volume and thickness at the end piece.

The field-flow fractionation technique, however, has been limited for certain operations because of the problem as to speed of operation and the loss of sample material by adhesion to the wall for the following reasons.

When a particle sample first enters a field-flow fractionation channel, it is generally distributed broadly over the channel cross-section. Before normal sample migration can occur, the components of the sample must undergo a relaxation process in which they approach a steady-state distribution within the channel, usually by accumulating near one channel wall. This process requires a finite time (typically from 10 seconds to 30 minutes) described by the relaxation time $\nu$. Because a good deal of band broadening can occur during the relaxation process, a stop-flow procedure is commonly used in which the flow through the channel is halted for a period of time $\nu$ in order to allow relaxation to occur under static conditions. The stop-flow procedure, generally required to avoid losses in resolution, is particularly essential for high flow rate runs. However, under any circumstances, stop-flow is an inconvenience and it consumes additional time for separation and often introduces baseline instabilities in sample detection. Sample losses due to adsorption or adhesion at the accumulation wall are also greatest during the stopflow period. Attempts to reduce the stopflow time by increasing the field strength only magnify the sample loss problem. Clearly, the development of a method to reduce relaxation effects and, where possible, eliminate the stop-flow procedure would represent an important advance in FFF techniques, particularly for high speed operations.

It is an object of the invention, therefore, to provide an improved FFF process which solves the above-noted problem as to relaxation time. It is a further object to provide a new FFF process which effects a reduction in the relaxation effect and where possible eliminates the stop-flow procedure. It is a further object to provide a modified FFF process which is capable of effecting separation at a very high rate of speed. It is a further object to provide a modified FFF process which can be adapted to any of the above-noted FFF techniques. These and other objects of the invention will be apparent from the following detailed description thereof.

SUMMARY OF THE INVENTION

It has now been discovered that these and other objects can be accomplished by the new process of the invention which presents for the first time an efficient process for reducing the relaxation effect and in many cases eliminates the stop-flow procedure which has limited the prior known FFF techniques.

The new process comprises an improvement in the FFF technique wherein a carrier fluid containing the particles to be separated is forced through a thin flow channel having an inlet and outlet end and a field or gradient is used to induce a driving force acting across the thin dimension perpendicular to the flow axis and the particles entering the channel at the inlet end undergo a relaxation process and approach a steady state distribution within the channel, the improvement comprising using as the thin channel one whose thickness is reduced at the inlet end relative to the thickness at the outlet end. Preferably the thin channel has a blocking element at the inlet end of the channel which reduces the thickness for a sufficient distance in the channel to largely complete the relaxation effect within that distance, after which the thickness increases to its normal value for the remaining length of the channel.

It has been surprisingly found that by the technique of reducing the channel thickness at the inlet end of the channel one can greatly hasten the relaxation process and in many cases eliminate the stop-flow procedure without a significant loss of resolution and thus greatly increase the speed of operation. In addition, as shown below the new technique is applicable to any and all of the above-noted FFF processes as indicated below.

The reduction in relaxation times can be put to use in three principal ways. First, if $v$ is short enough, a stopflow procedure is not necessary; injection without stopping or reducing flow rate is termed here stopless-flow injection. Second, injection and relaxation can proceed at a reduced (but not zero) flowrate to reduce sample losses to the wall. This is termed slow-flow injection. Third, even when stopflow is needed, the time delay before the initiation of FFF separation is reduced and the separation time is accordingly diminished.

It is important to note that a thin channel is generally desirable for the achievement of separation in FFF, as it is for the achievement of relaxation However, separation and relaxation are two relatively independent processes and the optimum channel thickness for one does not necessarily correspond to the optimum thickness for another. The present method allows the independent adjustment of channel thickness in two portions or segments of the channel, one optimized for separation and the other optimized for relaxation.

DESCRIPTION OF THE DRAWINGS

The various objects and features of the present invention can be more fully understood by reference to the accompanying drawings.

Referring to FIG. 1, the basic concept of FFF is represented by the flowrate vectors $\dot{V}$, associated flow vectors and the driving force vector F. These vectors are drawn in relation to two closely spaced parallel plate means, 10 and 12. The region between these plates is identified as a flow channel 14, through which the fluid is conducted. This fluid flow is represented by the flowrate vector $\dot{V}$ and by a velocity profile 16 which shows relative fluid movement by means of channel flow velocity vectors 18. The b is the breadth, L the length and w the thickness of the channel.

A primary driving force is imposed normal to the channel flow axis for the purpose of controlling the transverse positions of the particles. This driving force is illustrated as F oriented perpendicular to the channel flowrate vector $\dot{V}$ and the respective plate means. The plate means 12 is the channel wall toward which the particles are normally driven by the primary driving force and is termed the accumulation wall. The opposite channel wall defined by plate means 10 is termed the depletion wall.

Figure 1:
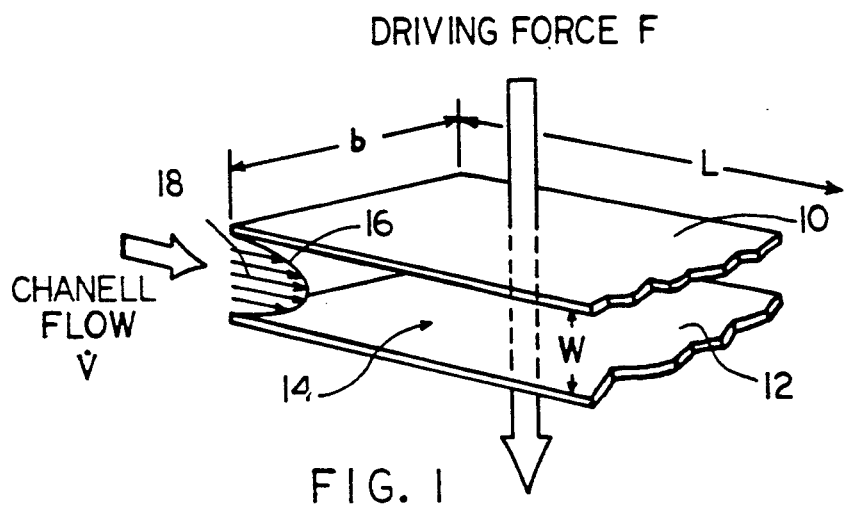
FIG. 1 shows a graphic, perspective view of a FFF flow channel depicting the flow and the field gradient applied.
Figure 2:
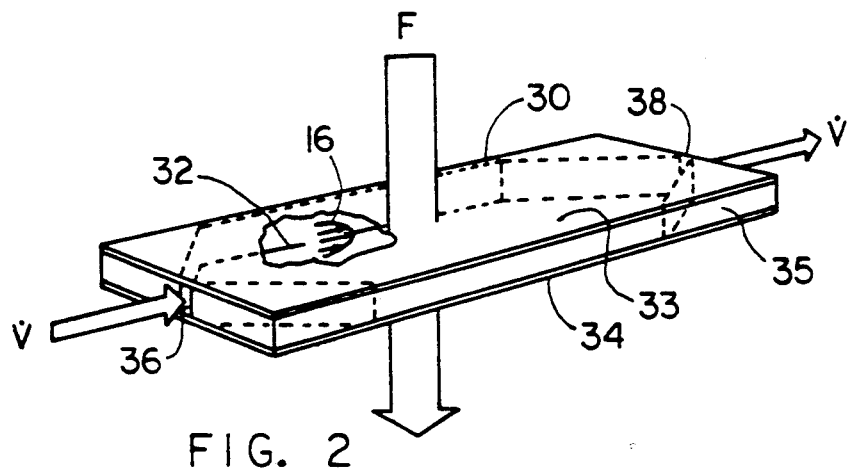
FIG. 2 depicts an FFF flow channel with enclosed structure around the channel.

The structure can be implemented by means of variations of basic elements. One example is shown in FIG. 2. The flow channel 32 is substantially defined by a first and second plate means 33 and 34. Side wall structures 30 and 35 provide the respective plate means to fully enclose the chamber region 32. A general configuration might comprise a spacer plate 35 having the desired thickness w interposed between respective nonpermeable or semi-permeable plates, the combination being tightly clamped together.

Inlet means 36 and outlet means 38 are provided at opposite ends of the chamber to enable channel flow there through. Flow control means associated therewith are desirable to facilitate adjustment of $\dot{V}$. Typically, the outlet end will feed effluent to detection means for obtaining separation results.

The inlet means consists of a narrower fluid inlet and a short tapered end piece usually roughly triangular in shape that serves to distribute the incoming flow smoothly out across the breadth of the channel.

Figure 3:
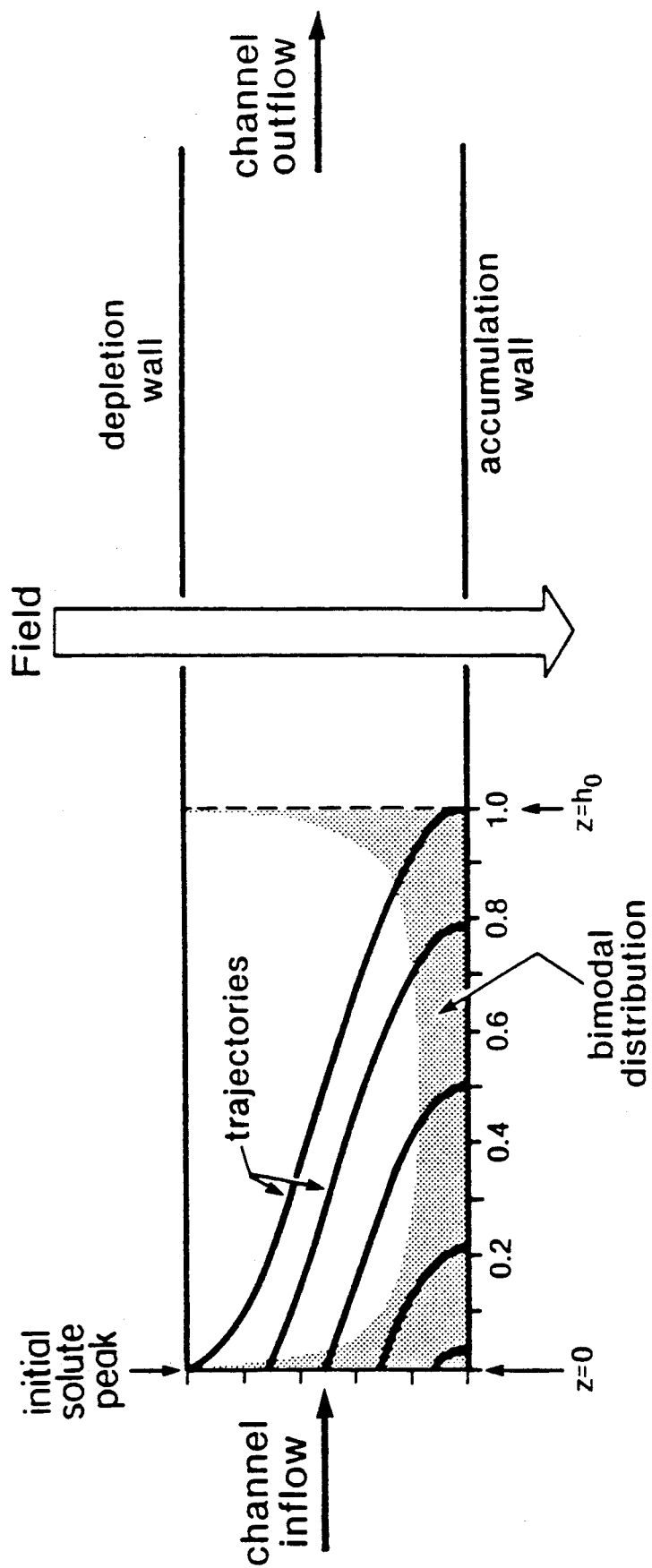
FIG. 3 is a graphic illustration of a side view of the channel showing the relaxation trajectories of particles and the resultant bimodal distribution of particles near the inlet of an FFF channel with stopless flow injections.

FIG. 3 is a sketch of the inlet end of an FFF channel showing how a narrow particle particle band is broadened in the course of relaxation. The parameter z is the distance along the axial coordinate, with the other components as described in the Figure.

Figure 4:
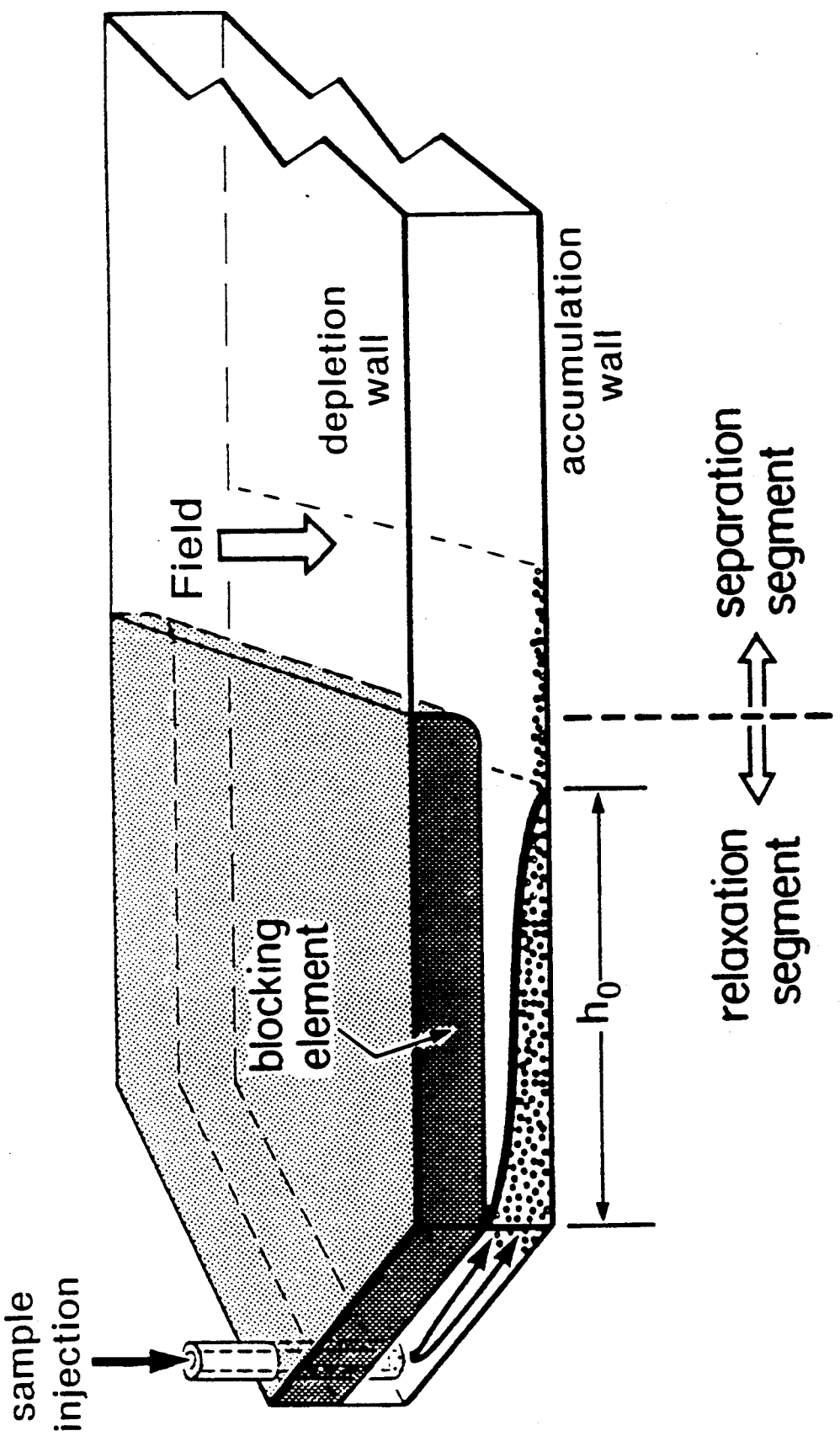
FIG. 4 is a graphic illustration of the structure of a pinched inlet channel for FFF. The relaxation process for one component is shown.

FIG. 4 is a graphic illustration of the pinched inlet concept with the blocking element being at the top or depletion wall of the channel at the inlet end.

Figure 5A:
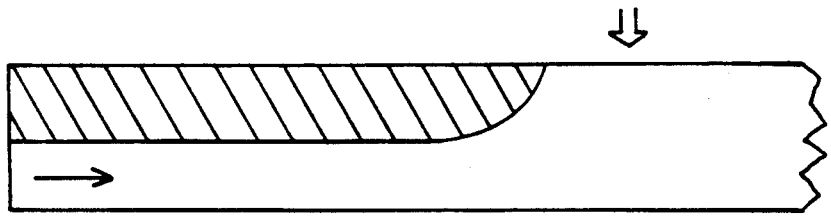
FIGS. 5A, 5B, 5C and 5D are graphic illustrations of various places where the blocking element or elements can be placed in the channel.
Figure 5B:
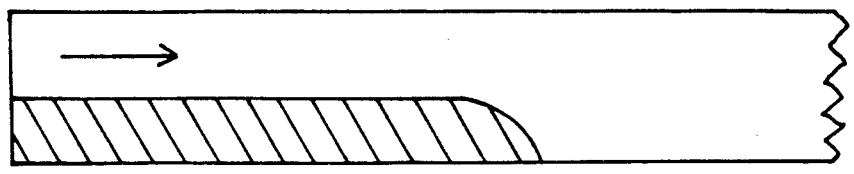
Figure 5C:
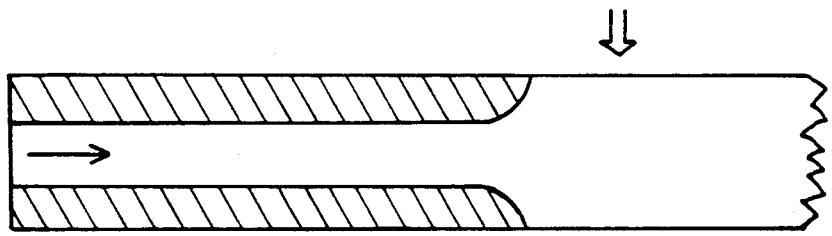
Figure 5D:
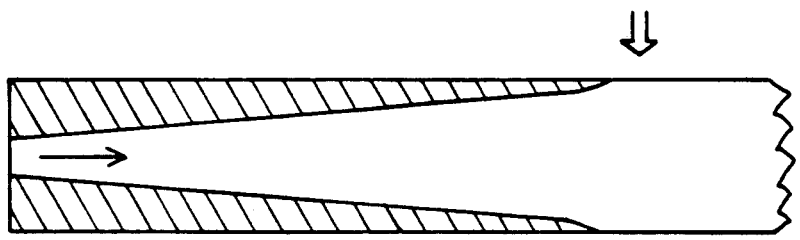

FIG. 5 is a graphic illustration showing some of the various positions in which the blocking element may be placed, such as in FIG. 5A at the top of the inlet end, FIG. 5B at the bottom of the inlet end of the channel, FIG. 5C at both the top and at the bottom of the inlet end of the channel, and FIG. 5D as a sloping blocking element at both the top and bottom walls.

Figure 6:
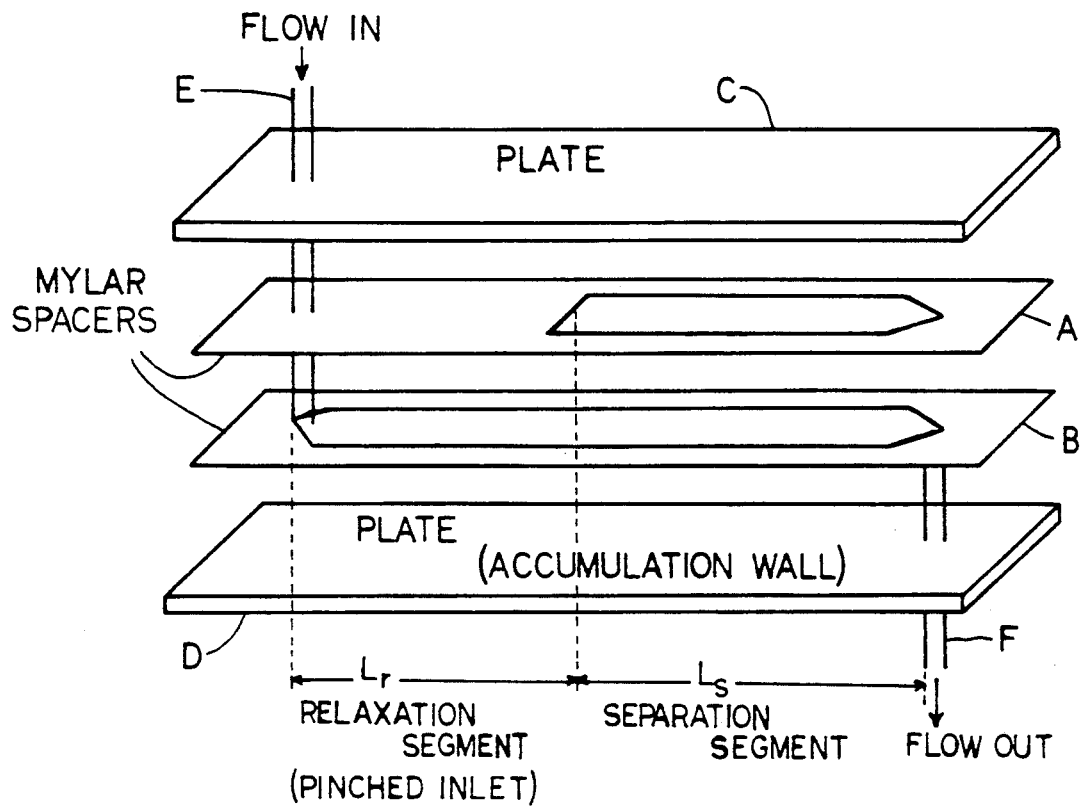
FIG. 6 shows how a blocking element can be put in place in an FFF channel using two differently cut spacer layers sandwiched between plates.

FIG. 6 is an illustration showing how a blocking element can be put in place in an FFF channel using two differently cut spacer layers A and B sandwiched between plates C and D. The resulting length of the relaxation segment or pinched inlet segment is shown as $L_r$ and the length of the separation segment or broadened section of the channel is shown as $L_s$. The inlet flow means is shown as E and the outlet flow means as F.

As noted FIG. 7 shows three different elution profiles for the polymer spheres used in the Example at the end of the specification.

DETAILED DESCRIPTION OF THE INVENTION

The implementation of the pinched inlet concept should be relatively simple as illustrated in FIG. 4. For channels having a sandwich construction in which the channel volume consists of a section cut out and removed from a spacer layer sandwiched between two wall layers, an appropriately segmented channel can be constructed by using two or more spacer layers from which volume elements of different lengths are removed. Thus, a channel like that in FIG. 4 can be made by sandwiching together two spacer elements between the primary walls of the system. A section of one spacer (termed blocking element) can be left intact while the corresponding region of the companion spacer can be removed to form the pinched segment of the channel volume as shown in FIG. 6. Alternatively, part or all of the segmentation might be produced by machining. The length $L_r$ of the relaxation segment is chosen in general such that most of the major components will undergo a major part, if not all, of their relaxation within this segment with continuous flow; $L_r > h_o$. This relaxation is shown for one component in FIG. 4. Clearly, $L_r$ and flow velocity are interrelated. For high speed stopless-flow operation with correspondingly large $\dot{V}$ and $h_o$ values, it is anticipated that the relaxation segment will occupy a substantial fraction of the total length of the channel system. Alternately, with slow-flow injection $L_r$ can be greatly reduced.

Flow in thin FFF channels is almost universally laminar. It is important that the flow in the transition region between segments maintains these laminar characteristics despite the rather abrupt change in cross section. Mixing currents at this point would have the potential to redistribute the component particles over the cross-section of the separation segment, in which case a second and less favorable relaxation process would be required. However, with smooth channel surfaces, a blocking element free of sharp edges and rough protrusions, and thin channel segments, effective flow laminarity should be achieved.

If the flow passing through the transition region were completely laminar, the transverse position of the blocking element would be immaterial. It could lie against the depletion wall, as shown in FIGS. 4 and 5A, or it could with equal effectiveness be layered against the accumulation wall as in FIG. 5B, or even divided into two layers, one adjacent to each wall as in FIG. 5C. However, the arrangement shown in FIG. 4 is preferred because the sample components, once concentrated at the accumulation wall, will be likely to proceed through the transition region without substantial perturbation even if flow disturbances are generated toward the interior of the channel.

It should be noted that the two-segment channel system shown in FIG. 4 has an initial portion preferably having a substantially uniform thickness, but could be replaced by a tapered channel that is relatively thin toward the inlet and thicker toward the outlet as shown in FIG. 5D. No distinct segments need exist. The general advantages of the method proposed here are expected from any such system no matter how the transition from the thin inlet region to the thicker outlet region is realized.

It should also be noted that an abbreviated relaxation step will generally occur after the component particles pass through the transition region. The expansion of the flow channel will lead to a comparable fractional expansion of the particle-containing lamina upon passage through the transition region; the steady-state concentration profile of particles may also change at the transition point. Thus, concentration re-equilibrium will be necessary after the transition region is passed. However, providing the particles are rather tightly confined in a thin laminae, most often adjacent to the accumulation wall, through the transition region, the readjustment necessary to the new steady-state conditions should be relatively brief and nondisruptive to the separation.

While in FIG. 4 a channel is shown with well-defined accumulation and depletion walls, under some circumstances different particles in the sample can go to opposing walls. This happens, for example, in sedimentation FFF when the carrier density is intermediate between that of two different particle populations. The pinched inlet concept will be equally applicable to this case providing proper attention is paid to the streamlining of the channel system in the transition region.

In general, wherever the channel is made thinner than at the outlet end, the additional wall material responsible for reducing the thickness, whether produced by machinery or by inserting thin films of material, is considered to be part of the blocking element or elements responsible for the pinched inlet configuration.

The pinched inlet method should constitute a useful modification to any field-flow fractionation system irrespective of field type, operating mode or channel geometry. However, special consideration will apply for each individual system. Some of these special considerations will be examined below for several subtechniques of FFF carried out in thin rectangular channels.

Sedimentation FFF

The application of the pinched inlet concept to sedimentation FFF should be straight forward. For a channel having a sandwich construction, the single spacer element normally used would only have to be replaced by two spacers, one of which would provide the blocking element as suggested in FIG. 4 and 6. However, in view of the strong centrifugal forces, it is important that the blocking element be sufficiently rigid or supported that it does not substantially sag into the channel space of the relaxation segment.

Alternately, if the density of a blocking element held at the inside wall is less than that of the carrier liquid, little channel distortion should be encountered because of buoyancy forces on the blocking element. Denser blocking elements might best be placed adjacent to the outside wall providing smooth laminar flow can be maintained through the transition region. In some cases it might be preferable to machine part or all of the channel volume out of one of the channel walls so that mechanical stability would be assured.

Thermal FFF

The primary challenge of thermal FFF is the thinness of the channel space; state-of-the-art channels are now typically 75 μm thick. To implement the pinched inlet concept without sacrificing the thinness of the separation segment, it would be necessary to utilize a blocking segment of extraordinary thinness, 25-50 μm. The thin spacer layer containing this blocking element could be made from a variety of materials. Both the uniformity of this layer and its thermal conductivity are important considerations. A highly conductive layer (e.g. made up of a film of metal) would lead to the highest temperature gradient in the relaxation segment of the channel and would thus give the fastest relaxation. Also the relaxation segment could be shortened in proportion to the reduction of $h_o$ resulting from the increase in U.

However, since a high conductivity blocking element would tend to give a high heat flux through the relaxation segment and possibly distort the temperature distribution elsewhere in the channel system, there would be some advantages to constructing the blocking element from a low conductivity layer of material, for example, one made of Mylar. The material should not have a heat conductivity appreciably lower than that of the carrier liquid; a value too low would not provide an adequate temperature gradient to drive the relaxation process.

Flow FFF

The following consideration should be give to applying the pinched inlet concept to flow FFF systems. The most uniform spacer materials for forming the blocking element are impermeable to flow, thus making normal crossflow difficult to realize in the relaxation segment. Without crossflow, relaxation would fail to occur. One solution is to use a thin membrane for the spacer forming the blocking element despite its greater nonuniformity. A second approach would involve using a tapered channel, perhaps formed around a spacer of continuously variable thickness. Alternately, a tapered channel or a channel with a blocking element like that shown in FIG. 4 might be partially or entirely machined out of the frit material forming the depletion wall, allowing a normal crossflow flux into the channel along its entire length. More specifically, the thickness of the relaxation segment might be provided by a spacer while the additional thickness of the separation segment could be machined from the depletion wall.

Another solution would entail using an asymmetric relaxation segment resembling asymmetric flow FFF channels previously developed (Wahlund, Giddings—J. C. Anal. Chem. 1987 59 1332).

Steric FFF

The pinched inlet strategy proposed here should be directly applicable to steric FFF applications. Here, too, the sample must be forced to one wall before normal migration can occur. Hydrodynamic lift forces will have some influence on relaxation but the net effect should not change substantially because under steady-state conditions the sample particles still occupy thin laminae usually near the wall.

By using stopless flow injection in steric FFF, continuous lift forces will be exerted on the sample particles. For the larger particles used in steric systems, the flow velocity can be adjusted to a value high enough to prevent the particles from adhering at the wall. Thus, a major problem of stop-flow injection, namely, particle adhesion to the accumulation wall, should be possible to circumvent. In flow/steric or flow/hyperlayer FFF, for example, it should be possible not only to avoid particle adhesion but to dispense with the membrane normally used at the accumulation wall and use only the rigid frit material supporting the membrane. Such a system would be simpler, more uniform in channel dimensions, and less prone to clogging.

Programmed Field FFF

The magnitude of relaxation effects in stopless flow FFF can be reduced by using programmed field FFF. These advantages are complemented and amplified by a pinched inlet system. It is noted that relaxation tends to occur faster in the case of programming because generally a higher initial field strength is used than in the nonprogrammed (isocratic)case. The disadvantage of this high initial field strength is that it can increase the adhesion of particles to the accumulation wall. On the basis of these favorable characteristics of programmed field operation, it should be possible to use stopless flow or slow flow injection to advantage in a majority of programmed runs.

The cases cited above where the use of a pinched inlet system would be advantageous are simply examples of its general utility in FFF operation. The same general advantages could be stated for electrical FFF, magnetic FFF, cyclical-field FFF, and other subtechniques and operating modes.

While the pinched inlet geometry will often reduce relaxationl zone broadening in stopless flow operation to acceptable levels, there are cases in which such zone broadening will still be excessive. Rather than using stop-flow injection in these cases, a slow-flow injection process (where relaxation occurs at reduced flow rates) could be used to bring relaxational broadening within acceptable limits.

The blocking element utilized in the thin channel can be of any suitable construction and any means of attachment to the channel walls. It may be incorporated directly in the wall or may be attached thereto by adhesives, etc. or incorporated as described herein above. The element can be prepared from any suitable material, such as plastic, metal, etc. and is often of the same type as used in the construction of the channel itself.

The thickness of the element will be as needed to effect the needed reduction in the relaxation effect. In general, with channels of a thickness varying from 50 to 500 $\mu$m, the thickness of the blocking element can preferably vary from about 25 to 75 percent of the channel thickness.

The length of the blocking element again should be sufficient to effect the above-noted purpose as to the reduction in the relaxation effect under stopless or slow flow conditions. In general, this will be from about 10% to 50% of the total length of the channel.

The conditions to be employed in the FFF systems are well known and fully illustrated in the prior art. For example, the type of particles, macromolecules and polymer molecules (all referred to herein as "particles") to be separated, the carrier fluids, the concentration of particles, the type of fields or gradients to be used, strength of field, temperature of separation, rate of flow, recovery techniques and general construction of the thin channels are all illustrated in Giddings—U.S. Pat. No. 4,737,268 and so much of that disclosure pertinent to the present invention is incorporated herein by reference.

To illustrate the operation of the presently claimed process and to compare the results obtained by that process over the conventional channel without the pinched inlet configuration, the following example is given.

COMPARATIVE EXAMPLE

The process employed was a steric FFF process using one conventional channel and two pinched inlet channels.

The channel volumes were cut out of thin plastic spacers and sandwiched between glass plates, then clamped together between polymethyl methacrylate bars. This general structure is useful for steric FFF using gravity as the driving force.

A Teflon spacer of 254 μm thickness was used for the uniform channel (lacking a pinched inlet). The channel, cut from the spacer, has a tip-to-tip length L of 38.4 cm and a breadth b of 2 cm. The void volume, measured as the elution volume of an unretained sodium benzoate peak, is 1.84 mL.

Two pinched inlet channels were constructed. Both utilized two sheets of Mylar in their construction, one with the full channel length removed and the other cut in such a way that a "blocking element" was left in place. The blocking element is a strip of material that occupies the inlet end of the channel in order to reduce its thickness and thus realize the pinched inlet geometry. The construction of the systems is illustrated in FIG. 6. The combined thickness of the two films is 254 μm in both cases, the same as the thickness of the uniform channel. For pinched inlet channel I, the two thicknesses are both 127 μm. For channel II, the film with the blocking element is 178 μm thick and the film from which the pinched inlet is cut is 76 μm thick. The length (38.4 cm) and breadth (2 cm) of the pinched inlet channel systems are identical to those used for the uniform channel. The length $L_r$ of the blocking element, measured from the channel tip to the blocking edge is 15.4 cm in both cases, 40% of the total channel length. The void volumes, also measured with a nonretained peak, are 1.52 mL for channel I and 1.41 mL for channel II.

The samples used in this study were polystyrene latex beads with mean diameters of 15 and 20 μm. The carried liquid was doubly distilled water with 0.01% FL-70 detergent and 0.02% sodium azide used as a bacteriocide. All runs were carried out at room temperature, 293±1 K. From 15 to 20 μL of the sample suspension (containing $2-3 \times 10^4$ particles) were injected into the channel through a septum by means of a microsyringe.

For the stopflow method the sample was slowly carried to the head of the channel with a Gilson Minipuls 2 pump. The flow was then completely stopped for a period adequate to allow the particles to relax to the accumulation wall. The relaxation time was calculated from the Stokes-Einstein equation. Following relaxation, flow was resumed.

In the case of stopless flow injection, the sample was introduced by syringe directly into the carrier stream. The flow of the latter was held constant, without change or interruption.

The eluted sample was monitored by a UV detector model UV-106, at a wavelength of 229 nm. A strip chart recorder was used to record the emerging peaks.

RESULTS

Figure 7A:
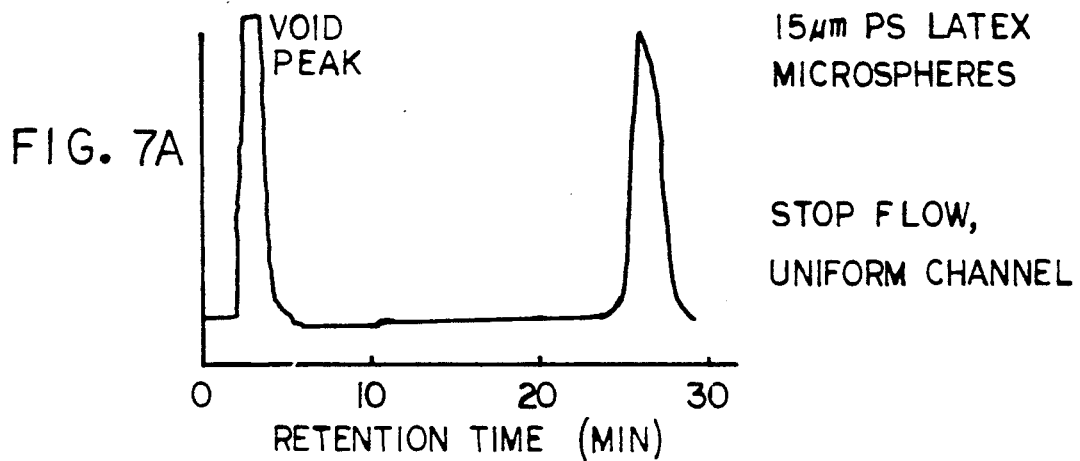
FIGS. 7A-7C show three different elution profiles for the polymer latex spheres used in the Example at the end of the specification.
Figure 7B:
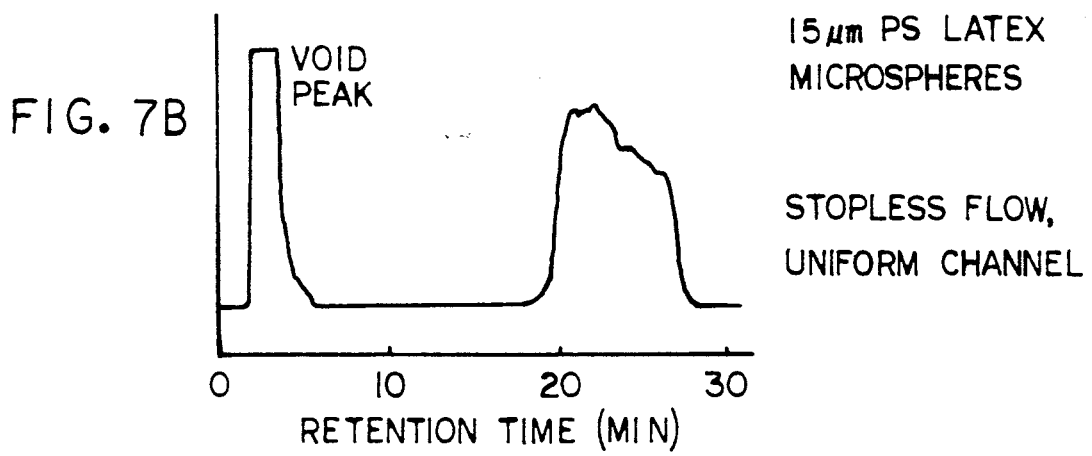
Figure 7C:
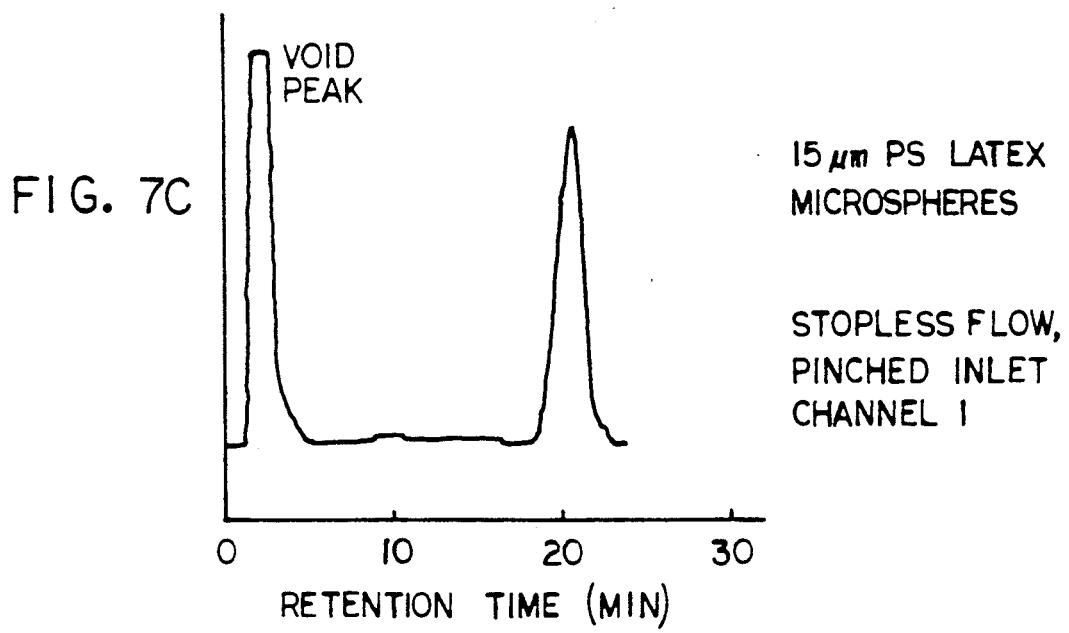

FIGS. 7A–7C show three different elution profiles for the 15 μm polystyrene latex spheres run at the same flow rates, 0.73 mL/min, equivalent to a linear flow velocity of 0.24 cm/s in the separation segment of the channel where the channel thickness (254 μm) is greatest. FIG. 7a shows the concentration profile of the particles emerging from the reference (nonpinched) channel after application of the stopflow procedure. For this case, the stopflow time was 42 s, equal to the calculated relaxation time of the particles across the full channel thickness (254 μm). FIG. 7b shows the results of a run identical in all respects to that of FIG. 7a except that the stopflow procedure was used to bypass the flow interruption of stopflow. The emerging peak in this case shows a substantial loss of sharpness as expected for stopflow operation. (For smaller particles with longer relaxation times than that of the 15 μm particle, the stopflow profile would be much broader and would have a bimodal shape.) We also observe that the trailing edge of the peaks in FIGS. 7a and 7b nearly coincide in their positions, the leading edge of the FIG. 7b profile, however, appears considerably earlier than that for the FIG. 8a peak as a consequence of the accelerated elution of those particles starting the run near the top wall of the channel where relaxation effects are maximal.

FIG. 7c shows the profile of the 15 um beads emerging from pinched inlet channel System I after stopless flow injection. We observe that the excessive band broadening illustrated by FIG. 7b has been eliminated through the use of the pinched inlet channel. The band width is comparable to that in FIG. 8a for normal stopflow operation. More specifically, the standard deviation $\delta_t$ in times units for the three profiles are 0.86, 2.35 and 0.77 s for FIGS. 7a, 7b and 7c, respectively. The corresponding plate heights are 0.43, 3.7 and 0.52 mm, respectively.

It is noted that to fully utilize the capabilities of the pinched inlet channel system, the flowrate must be matched to the dimensions of the pinched inlet segment in order to assure complete relaxation of all components before they enter the second stage, the separation segment. The flowrate used in conjunction with FIGS. 7A–7C accordingly yields an $h_o/L$ value of 0.26, well below the maximum allowable value of 0.4, equal to the ratio of the length of the pinched segment to the total channel length.

Related results are found for the 20 μm polymer particles.

I claim as my invention:

1. In a FFF process wherein a carrier fluid containing particles to be separated flows through a thin flow channel having an inlet end and an outlet end and further wherein a field or gradient is used to induce a driving force on the particles in a direction across the thin dimension perpendicular to the flow axis, the improvement comprising reducing the thickness of an initial portion of the channel extending from the inlet end downstream for a distance of from 10% to 50% of the total distance between the inlet end and outlet end of said channel, so that the initial portion of said flow channel has a substantially uniform thickness that is from about 25% to 75% of the thickness of the channel downstream from the initial portion.

2. The improvement in a FFF process in accordance with claim 1, wherein the thickness of the channel downstream from said initial portion is between about 50 μm and 500 μm.

3. The improvement in a FFF process in accordance with claim 1, wherein the initial portion of said channel has a substantially uniform thickness that is between about 33% to 67% of the thickness of the channel downstream from said initial portion.

4. The improvement in a FFF process in accordance with claim 1, wherein the thickness of the initial portion of the channel is reduced by a blocking element positioned in the initial portion of said channel, said blocking element having a substantially uniform thickness that is from about 25% to 75% of the thickness of the channel.

5. The improvement in a FFF process in accordance with claim 1, wherein the field or gradient is selected from the group consisting of gravitation, centrifugation, dielectric fields, electrical fields, cross flow forces, temperature gradient, density gradient, pH gradient, concentration gradient and combinations thereof.

6. An apparatus for separating mixtures of particles contained in a fluid stream into desired fractions comprising a thin flow channel having a top wall, a bottom wall, two side walls, an inlet end possessing an inlet means and an outlet end possessing an outlet means, means for applying a field or gradient having at least a component thereof along the top wall perpendicular to the plane of any flow stream within the channel, and means including a blocking element for reducing the thickness of the channel between the top wall and bottom wall at an initial portion of said channel, said initial portion extending from the inlet end toward the outlet end for a distance of from 10% to 50% of the total length of the channel between the inlet end and the outlet end, so that the initial portion of said flow channel in which the blocking element is located has a substantially uniform thickness that is from about 25% to 75% of the thickness of the channel downstream from the initial portion.

7. Apparatus in accordance with claim 6 wherein the thickness of the channel downstream from said initial portion is between about 50 $\mu$m and 500 $\mu$m.

8. The apparatus in accordance with claim 6, wherein the initial portion of said channel has a substantially uniform thickness that is between about 33% to 67% of the thickness of the channel downstream from said initial portion.

9. An apparatus for separating mixtures of particles contained in a fluid stream into desired fractions comprising a thin flow channel having a top wall, a bottom wall, two side walls, an inlet end possessing an inlet means and an outlet end possessing an outlet means, means for applying a field or gradient having at least a component thereof along the top wall perpendicular to the plane of any flow stream within the channel, and at least one blocking element at the inlet end, said blocking element having a substantially uniform thickness that is from about 25% to 75% of the thickness between the top wall and bottom wall of said channel, said blocking element extending from the inlet end toward the outlet end for a distance of from 10% to 50% of the total length of the channel between the inlet end and the outlet end, so that an initial portion of said flow channel in which the blocking element is located has a substantially uniform thickness that is from about 25% to 75% of the thickness of the channel downstream from the initial portion.

10. Apparatus in accordance with claim 9, wherein the blocking element is attached to or an integral part of the top wall of the channel at the inlet portion of the channel.

11. Apparatus in accordance with claim 9, wherein the blocking element is attached to or an integral part of the bottom wall of the channel at the inlet portion of the channel.

12. Apparatus in accordance with claim 9, wherein there are two blocking elements, with the first blocking element being attached to or an integral part of the top wall of the channel at the inlet portion of the channel, and with the second blocking element being attached to or an integral part of the bottom wall of the channel at the inlet portion of the channel.

13. Apparatus in accordance with claim 9, wherein the means for applying the field or gradient is a means for applying a driving force or gradient selected from the group consisting of gravitation, centrifugation, dielectric fields, electrical fields, cross flow forces, temperature gradient, density gradient, pH gradient, concentration gradient and combinations thereof.

* * * * *